United States Patent
Naczynski et al.

(10) Patent No.: US 10,814,017 B2
(45) Date of Patent: *Oct. 27, 2020

(54) MULTIFUNCTIONAL INFRARED-EMITTING COMPOSITES

(71) Applicant: Rutgers, The State University of New Jersey, New Brunswick, NJ (US)

(72) Inventors: Dominik J. Naczynski, Wallington, NJ (US); Mei-Chee Tan, Singapore (SG); Richard E. Riman, Piscataway, NJ (US); Charles Roth, Princeton, NJ (US); Prabhas V. Moghe, Basking Ridge, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,792

(22) Filed: Apr. 9, 2019

(65) Prior Publication Data

US 2019/0231905 A1  Aug. 1, 2019

Related U.S. Application Data

(63) Continuation of application No. 14/115,752, filed as application No. PCT/US2012/036852 on May 7, 2012, now Pat. No. 10,286,088.

(60) Provisional application No. 61/483,128, filed on May 6, 2011, provisional application No. 61/482,668, filed on May 5, 2011.

(51) Int. Cl.
| | |
|---|---|
| *A61K 49/00* | (2006.01) |
| *A61B 5/00* | (2006.01) |
| *A61B 5/055* | (2006.01) |
| *A61B 6/00* | (2006.01) |

(52) U.S. Cl.
CPC ........ *A61K 49/0065* (2013.01); *A61B 5/0075* (2013.01); *A61K 49/0019* (2013.01); *A61K 49/0093* (2013.01); *A61B 5/055* (2013.01); *A61B 6/481* (2013.01); *A61B 6/5247* (2013.01)

(58) Field of Classification Search
None
See application file for complete search history.

(56) References Cited

U.S. PATENT DOCUMENTS

| | | |
|---|---|---|
| 5,319,203 A | 6/1994 | Anderson et al. |
| 5,455,489 A | 10/1995 | Bhargava |
| 5,541,012 A | 7/1996 | Ohwaki et al. |
| 5,698,397 A | 12/1997 | Zarling et al. |
| 6,039,894 A | 3/2000 | Sanjurjo et al. |
| 6,699,406 B2 | 3/2004 | Riman et al. |
| 7,094,361 B2 | 8/2006 | Riman et al. |
| 2004/0125459 A1 | 7/2004 | Tanitsu et al. |
| 2005/0061982 A1 | 3/2005 | Ichinose et al. |
| 2007/0269382 A1 | 11/2007 | Santra et al. |
| 2009/0081461 A1 | 3/2009 | Yi et al. |
| 2009/0104212 A1 | 4/2009 | Bourke |
| 2010/0099779 A1 | 4/2010 | Hnojewyj et al. |
| 2010/0320480 A1 | 12/2010 | Rapoport et al. |

OTHER PUBLICATIONS

Chatterjee et al. Upconversion fluorescence imaging of cells and small animals using lanthanide doped nanocrystals. 2008 Biomaterials 29: 937-943. (Year: 2008).*
Wang, et al. "Hydrothermal Synthesis of Rare-Earth Fluoride Nanocrystals." Inorg. Chem. 45: 6661-6665. (2006).
Tan, et al. 'Near Infrared-Emitting Er- and Yb—Er-Doped CeF3 Nanoparticles with no Visible Upconversion', Aug. 2009, Optics Express, vol. 17, No. 18, pp. 15904-15910.
Naczynski, et al: "Albumin Nanoshell Encapsulation of Near-Infrared-Excitable Rare-Earth Nanoparticles Enhances Biocompatibility and Enables Targeted Cell Imaging", Small, 2010, vol. 6, No. 15, pp. 1631-1640.
Zhao, et al: "Surface-Modified Shortwave-Infrared-Emitting Nanophotonic Reports for Gene-Therapy Applications", ACS Biomaterials Science & Engineering, 2018, vol. 4, pp. 2350-2363.
Wu, et al: "pH-Responsive Quantum Dots via an Albumin Polymer Surface Coating", J. Am. Chem. Soc., 2010, vol. 132, pp. 5012-5014.
Anhorn, et al: "Specific Targeting of HER2 Overexpressing Breast Cancer Cells with Dororubicin-Loaded Trastuzumab-Modified Human Serum Albumin Nanoparticles", Bioconjugate Chem., 2008, vol. 19, pp. 2321-2331.
Xie, et al: "PET/NIRF/MRI Triple Functional Iron Oxide Nanoparticles", Biomaterials, 2010, vol. 31, pp. 3016-3022.

* cited by examiner

*Primary Examiner* — Jennifer Lamberski
(74) *Attorney, Agent, or Firm* — Fox Rothschild LLP

(57) ABSTRACT

Disclosed is a method of non-invasive infrared imaging, comprising (a) administering a composition containing infrared-emitting particles which contain rare earth elements that emit in the short-wavelength infrared (SWIR) spectrum, where the particles are encapsulated with a biocompatible matrix to form downconverting encapsulated particles; and (b) irradiating with infrared radiation, where both excitation and emission spectra of the encapsulated particles are in the infrared region. Analogous methods of image-guided biomedical intervention, and drug tracking and delivery are also disclosed. Also disclosed is a composition for biomedical applications, containing infrared-emitting particles which contain rare earth-elements that emit in the short-wavelength infrared (SWIR) spectrum, where the particles are encapsulated with a biocompatible matrix to form downconverting encapsulated particles.

21 Claims, 10 Drawing Sheets

MULTIFUNCTIONAL INFRARED-EMITTING COMPOSITES

CROSS-REFERENCE TO RELATED APPLICATIONS

The present application is a Continuation of U.S. Non-Provisional application Ser. No. 14/115,752, filed on Mar. 10, 2014, which is a U.S. National Phase of International Patent Application Serial No. PCT/US12/36852, filed May 7, 2012, which claims the benefit of priority under 35 U.S.C. § 119(e) of U.S. Provisional Application Ser. Nos. 61/483,128, filed on May 6, 2011, and 61/482,668, filed on May 5, 2011, the entire disclosures of which are incorporated herein by reference.

The present application is also related to U.S. Ser. No. 13/466,079, filed on May 7, 2012.

STATEMENT REGARDING FEDERALLY SPONSORED RESEARCH OR DEVELOPMENT

The invention was made with government support under Contract No. NIRT 0609000, awarded by the National Science Foundation. The government has certain rights to this invention.

BACKGROUND OF THE INVENTION

It is increasingly recognized that molecular and cellular imaging approaches are needed to provide a personalized portrait of disease states and to track responses to therapeutic regimens. Currently, the use of visible-light excitable fluorophores is limited due to poor tissue penetration and autofluorescence caused by the excitation light.

The present invention is directed to the downconversion properties of the specifically coated rare earth materials. The current state of the art has been focused exclusively on the upconversion properties of rare earths. Applicants now discovered that certain coated rare earth materials can be specifically tuned to optimize shortwave infrared emissions for the purpose of non-invasive infrared imaging applications. Biomedical infrared imaging (i.e., where both excitation and emission is in the infrared) has not heretofore been utilized by either the rare earth or biomedical imaging communities.

BRIEF SUMMARY OF THE INVENTION

It has now been discovered that fluorescence generated by the excitation of Rare Earths, hereinafter REs, such as Yb—Er co-doped $NaYF_4$ nanoparticles, with near infrared light avoids these shortcomings, providing highly useful luminescence for biological imaging. We disclose a novel approach for fabricating water dispersible and biologically targeted REs by encapsulation of the particles in human serum albumin nanoshells (RE-ANSs). The encapsulation reduced the cytotoxicity of the REs while providing surface groups for conjugating targeting ligands. RE-ANSs modified with cyclic-RGD (cRGD) targeted αVβ3 integrin receptors overexpressed on U87 glioblastoma cells with minimal targeting of low αVβ3-expressing cells. Furthermore, upon intravenous injection into mice exhibiting melanoma, the emission of the RE-ANSs in the 1.5-1.6 μm spectral range can be visualized in lesions throughout the animal using an InGaAs camera. Additional modification of the carriers by therapeutic encapsulation creates multifunctional nanoparticles for both imaging and drug delivery applications. Our results indicate that RE-ANSs are suitable for imaging cancer cells, as we all for combined imaging and targeted drug delivery in vivo.

One embodiment of the invention is directed to methods of preparation of rare earth-based light-emitting multifunctional composites, and their use in biomedical applications, such as non-invasive imaging (2-dimensional and 3-dimensional), image-guided interventions (surgical and non-surgical), drug tracking and delivery and photodynamic therapy applications. In contrast to current optical imaging contrast agents, these infrared-emitting rare earth composites are activated by near infrared sources (700 to 1000 nm) to emit also in the shortwave infrared (e.g. 1000 to 2500 nm) and visible wavelength radiation ranges (400 to 700 nm). The infrared-emitting composites comprise of one or more infrared-emitting rare earth doped nanoparticles encapsulated within a biocompatible polymer, polypeptide, polysaccharide or macromolecule (e.g., deoxyribonucleic acid, ribonucleic acid, proteins, glycoproteins). The size range of these composites can be tailored from 20 nm to 10 μm, and can be modified using different polymers, polysaccharides, polypeptides or macromolecules to control the in vivo bio-distribution. Various embodiments of the invention serve multifunctional utility in a variety of therapeutic management strategies. For therapeutic applications, the composite can also serve as a drug carrier (drug refers to any pharmacologic factor such as a small bioactive molecule or gene or biologic), where the biophotonic properties of the carrier can be used to track the drug distribution and release or to actuate drug release by light emitted from the rare earth nanoparticles or controlled by the polymer, polysaccharide, polypeptide or macromolecule degradation. Further functionality to the composite can be added by modifying the surfaces with targeting ligands to localize these carriers to specific sites of interest.

One embodiment of the present invention is directed to a method of non-invasive infrared imaging, comprising the steps of:
 (a) administering a composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and
 (b) irradiating with infrared radiation,
 wherein both excitation and emission spectra of the coated nanoparticles are in the infrared region.

Another embodiment of the invention is directed to a method of image-guided biomedical intervention, comprising the steps of:
 (a) administering a composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and
 (b) irradiating with infrared radiation,
 wherein both excitation and emission spectra of the coated nanoparticles are in the infrared region.

Still another embodiment of the invention is directed to a method of drug tracking and delivery, comprising the steps of:
 (a) administering a drug composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and (b) irradiating with infrared radiation, wherein both excitation and emission spectra of the coated nanoparticles are in the infrared region.

Another embodiment of the invention is directed to a method of improving the biocompatibility and/or reducing the toxicity and/or side effects of a drug and/or imaging agent, comprising the step of encapsulating the drug and/or imaging agent with a biocompatible matrix.

Yet another embodiment of the invention is directed to a method of biologically targeting a drug and/or imaging agent, comprising the step of encapsulating the drug and/or imaging agent with a biocompatible matrix.

For any of the above methods, a preferred biocompatible matrix comprises human serum albumin (HSA). In addition, for any of the above methods, the biocompatible matrix can further comprise a pharmaceutical agent, and/or a targeting molecule which directs the coated nanoparticle to a biological target. A preferred targeting molecule comprises cyclic arginine-glycine-aspartic acid (cRGD) tripeptide.

For the methods comprising nanoparticles, the nanoparticles preferably comprise $CeF_3$ doped with one or more rare earth elements selected from the group consisting of Yb, Nd, Tm, Er, Pr, Dy and Ho. Most preferably the rare earth elements are selected from the group consisting of Pr, Nd, Yb and Er. In addition, for the methods comprising nanoparticles, the nanoparticles can further comprise one or more elements selected from the group consisting of Gd, La, Ce, Pm, Sm, Eu, Gd, Tb, and Lu. This allows for use as a multi-modal imaging agent. The multi-modal detection scheme can be selected from optical/MRI, or optical/PET with a radiolabel.

Yet another embodiment of the invention is directed to a composition for biomedical applications, comprising infrared-emitting nanoparticles comprising rare earth-elements, wherein the nanoparticles are encapsulated with a biocompatible matrix to form downconverting coated nanoparticles tuned to optimize short-wavelength infrared (SWIR) emission. Preferably the biocompatible matrix comprises human serum albumin (HSA). Also, the biocompatible matrix can further comprise a pharmaceutical agent, and/or a targeting molecule which directs the coated nanoparticle to a biological target. A preferred targeting molecule comprises cyclic arginine-glycine-aspartic acid (cRGD) tripeptide. As above, the nanoparticles preferably comprise $CeF_3$ doped with one or more rare earth elements selected from the group consisting of Yb, Nd, Tm, Er, Pr, Dy and Ho. Most preferably the rare earth elements are selected from the group consisting of Pr, Nd, Yb and Er. In addition, the nanoparticles can further comprise one or more elements selected from the group consisting of Gd, La, Ce, Pm, Sm, Eu, Gd, Tb, and Lu. This allows for use as a multi-modal imaging agent. The multi-modal detection scheme can be selected from optical/MRI, or optical/PET with a radiolabel.

DETAILED DESCRIPTION OF PREFERRED EMBODIMENTS

Figure 1:
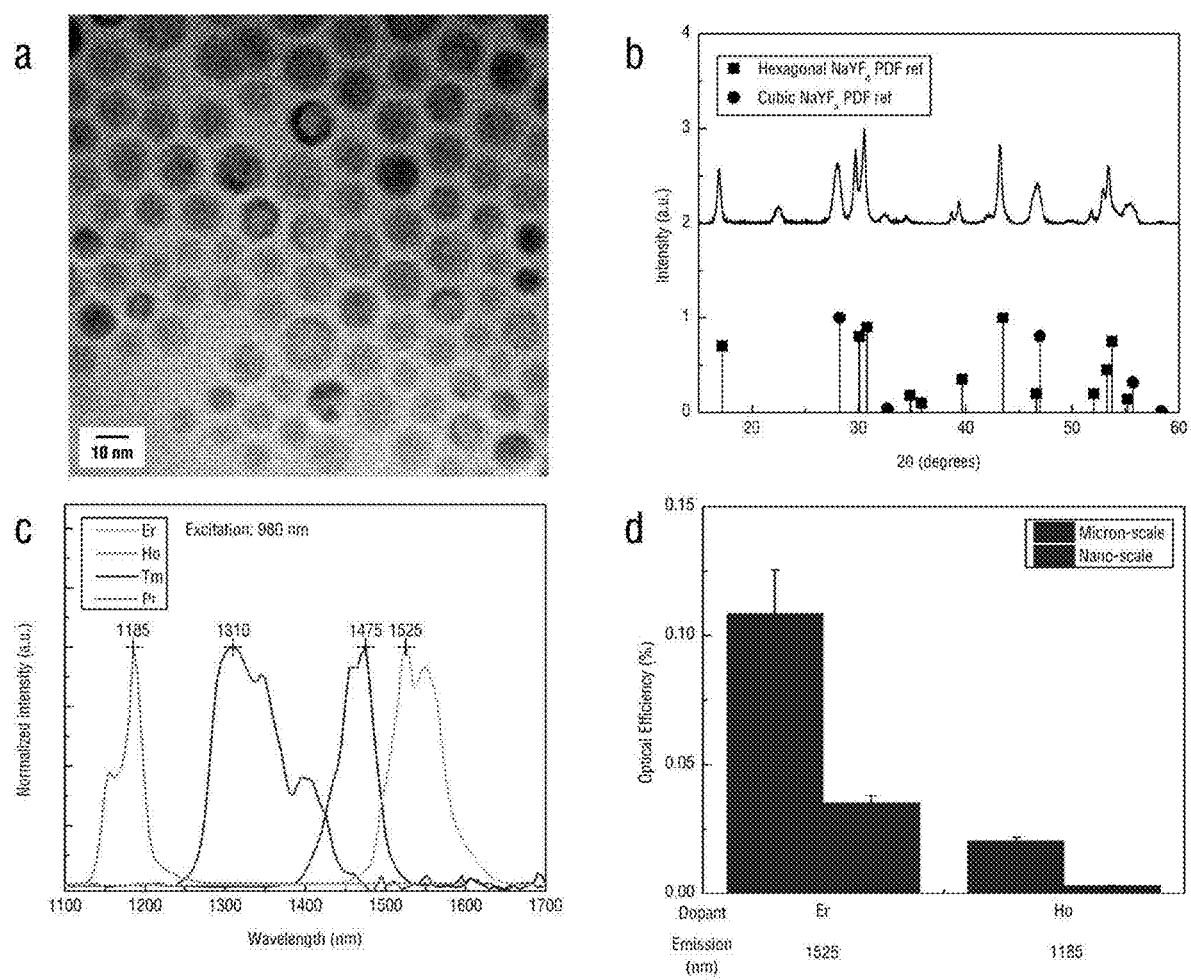
FIG. 1 shows physical and optical properties of REs.

Rare Earth (RE) Nanoparticles as a Superior Modality as an IR-Emission Platform

Using REs for 2- and 3-dimensional non-invasive imaging presents several unique, competitive advantages over conventional imaging agents. The wavelengths of emissions can be tailored by controlling the nature and concentration of the dopant and host. Infrared excitation enables deeper tissue penetration depths and low background tissue autofluorescence. Also, since there is no overlap between the excitation and emission wavelengths, images with high signal-to-noise ratio can be collected using RE nanoparticles. The extent of infrared light propagation and the volumetric energy distribution of infrared light are governed by the absorption and scattering properties of tissues. Major tissue absorbers of infrared light are hemoglobin, melanin and water, while composition, size and morphology of tissue components control the light scattering. Infrared light has been reported to travel through 10 cm of breast tissue and 4 cm of skull tissue using microwatt sources. Based on the absorption properties, the attenuation coefficients of oxygenated blood in the visible and infrared regions are 500 and 30 cm$^{-1}$, respectively, which corresponds to attenuation length of 0.002 and 0.03 cm where the intensity of the beam has dropped to 1/e. Therefore, infrared light can reach penetration depth of up to almost 10 times that of visible light. Most REs can be tuned to emit in both the visible and infrared regions (see FIG. 1). Using infrared emissions for imaging have been reported to improve imaging sensitivity by up to ~10 times. In addition, REs are more stable than organic dyes, showing almost no loss in emission intensities over time (e.g. 30-60 days). In comparison, most organic dyes suffer from poor photostability, which results in reducing emission intensities after a day. Alternative possible infrared-emitting inorganic substitutes like HgTe and $Cd_xHg1_xTe$, InP and InAs, and PbS, PbSe, and PbTe comprise several well-known toxic elements, and are thus not favorable for biomedical applications. Weakly infrared emitting carbon nanotubes and gold particles have broad emission peaks (i.e. bandwidth >>100 nm) and typically require an optimal excitation in the visible region or high power pulsed excitation sources (~20 W). In contrast, the optimal excitation of rare earth nanoparticles have narrow emission bandwidths (<100 nm) and can be tuned to be excited within the MR window using low power continuous wave sources (<2 W).

Rare Earth/Biocompatible Matrix Composites

A drug delivery composite platform that utilizes near infrared both "upconversion" and "downconversion" fluorescence, providing highly useful luminescence for biological imaging both in vitro and in vivo has been discovered. The final encapsulated composite material is stable in aqueous solution, highly biocompatible and is amenable to fluorescence imaging with high fidelity. Biocompatibility is conferred or enhanced by coating the particles with a biocompatible matrix. Enhanced biocompatibility can be manifested in reduced in vitro or in vivo toxicity. In one embodiment of the invention, rare earth-containing particles, preferably nanoparticles (REs) are encapsulated to form rare earth-containing particles coated with an biocompatible matrix that is optically transparent. Optical transparency of the matrix is important to the excitation and emission properties of the composites. Encapsulation can result in the coating of a single particle, or can be adjusted by those skilled in the art to provide encapsulated composites comprising a plurality of particles encapsulated in a nanoshell. The particle loading in such a particle encapsulate can be 0.004 to 94 weight % (0.001 to 80 volume %). A composite comprising a multiparticle microcapsule is preferred for biomedical applications due to the phonon-assisted energy transfer between the particles.

The ratio of the biocompatible matrix to rare earth-containing particles can be adjusted based on the desired therapeutic action. The multiparticle microcapsule can comprise a low concentration of heavily rare earth-doped particles, or a high concentration of lightly rare earth-doped particles. Conversely, the multiparticle microcapsule can comprise a low concentration of lightly rare earth-doped particles, or a high concentration of heavily rare earth-doped particles. For biomedical applications the highest weight percent load of particles in the matrix is generally about 10 to 40 weight % (2.6 to 13.7 volume %).

The biocompatible matrix can be covalently bound to the particles, or non-covalently associated.

Preferably the optically transparent biocompatible matrix comprises an albumin nanoshell ((RE)ANS). The rare earth-containing particles themselves have a particle size between 2 nm and 100 micrometers (microns), preferably between 5 nm and 10 micrometers, more preferably between 10 nm and 1 micrometer, most preferably between 10 nm and 500 nm. Nanoparticles are preferred. Encapsulation of particles can be achieved using controlled coacervation of the biocompatible matrix, for example, human serum albumin (HSA), in an aqueous solution to provide multiparticle microcapsules having a particle size between 5 nm and 100 micrometers, preferably between 10 nm and 1 micrometer, more preferably between 10 nm and 500 nm, and most preferably between 100 nm and 300 nm (see FIGS. 1 and 2). One skilled in the art can elect the size of the particle encapsulate/multiparticle microcapsule based on the desired therapeutic action. The particles to be encapsulated are smaller than the multiparticle microcapsule. In some embodiments the particles to be encapsulated are about a factor of 10 or more smaller than the multiparticle microcapsule. Nanoparticle encapsulates are generally preferred.

In order to form the particles of the invention, host particles are doped with at least one rare earth element that emits in the short-wavelength infrared (SWIR) spectrum. The SWIR spectrum covers the wavelength range of about 1.4 to about 3 micrometers (microns). The rare earth doping concentration can be as low as 1 ppb, and as high as the concentration where concentration or quantum quenching begins, which depends on both the host particle and the rare earth element, but is generally about 7.5 mole percent at the high end (for example, Yb in $CeF_3$). The rate at which concentration quenching begins is readily determined by those skilled in the art. Preferably the doping concentration ranges between 1 ppm and 5 mole percent. More preferably the doping concentration ranges between 1000 ppm and 5 mole percent. Still more preferably the doping concentration ranges between 0.1 and 3 mole percent. Most preferably the doping concentration ranges between 0.5 and 1 mole percent. Preferably the host is a low phonon-energy material. A preferred host is $CeF_3$. U.S. application Ser. No. 13/466,079 discloses preferred rare earth-doped particles, and is incorporated herein by reference in its entirety.

The doped particles of the invention are preferably highly chemically uniform in terms of the distribution of the rare earth element(s) in the host. This prevents localized concentration quenching. One method of uniform synthesis is taught in D. J. Naczynski, T. Andelman, D. Pal, S. Chen, R. E. Riman, C. M. Roth, P. V. Moghe, "Albumin nanoshell encapsulation of near infrared excitable rare-earth nanoparticles enhances biocompatibility and enables targeted cell imaging", *Small*, 6 [15] 1631-1640 (2010), the entire disclosure of which is incorporated herein by reference.

Figure 2:
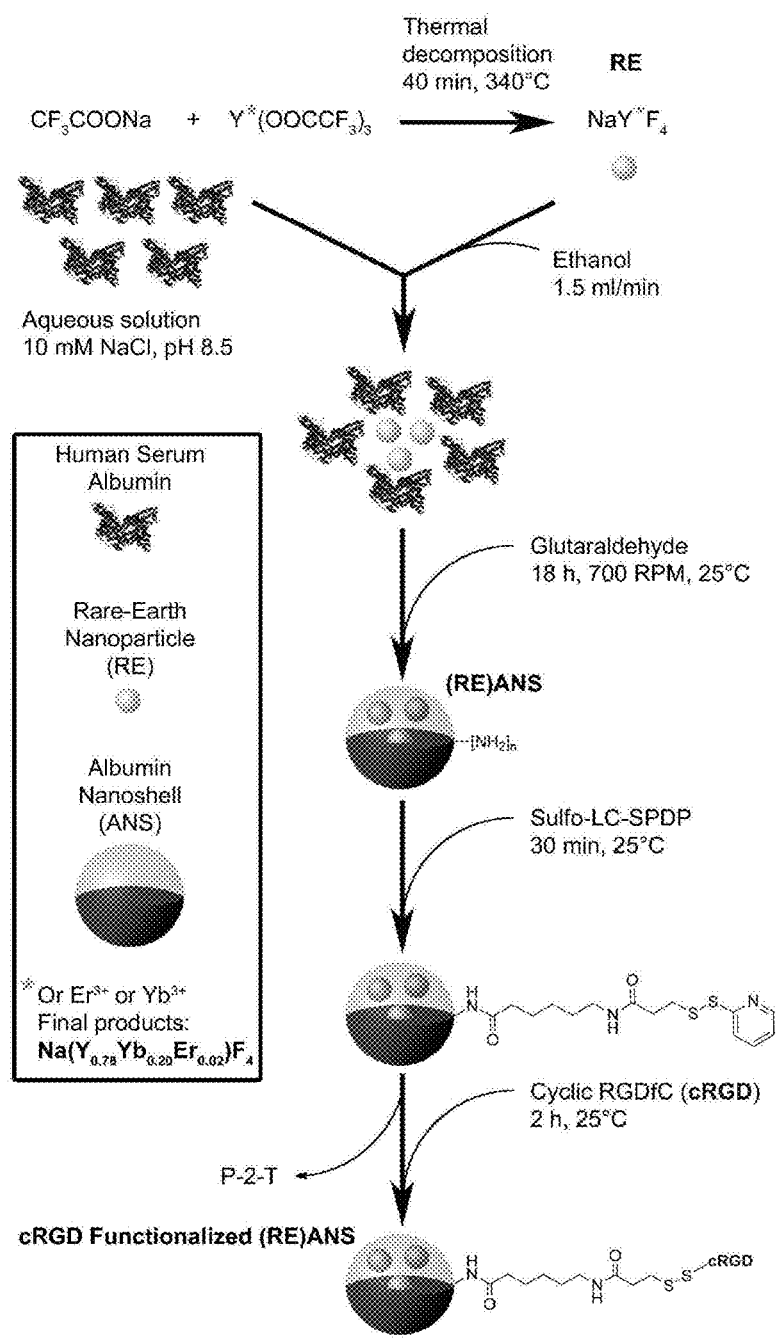
FIG. 2 displays a schematic representation of the method of albumin encapsulation of rare earth nanoparticles.

The crystalline phase of the particles is selected which results in the greatest intensity emission. This is readily done by those skilled in the art. FIG. 1 shows the physical and optical properties of REs. The TEM images of REs (a) show uniform 10 nm spherical particles. X-ray crystallography (XRD) plot of REs show a predominately hexagonal phase crystalline structure (b). Hexagonal phase REs exhibit the most efficient and intense SWIR emissions. The SWIR (c) emission of REs can be tuned by changing the types of rare earth dopant used during synthesis. REs consisting of a $NaYF_4$ host doped with ytterbium (Yb) and one or more elements selected from erbium (Er), holmium (Ho), thulium (Tm) and praseodymium (Pr) are favored for their low phonon energies that minimize non-radiative losses to enable intense emission spanning the SWIR region. The optical efficiency of a specific dopant scheme can be further tuned by varying the particle size of the $NaYF_4$ host. Generally, larger, micron sized $NaYF_4$ host exhibits greater SWIR emission than their nanoscale counterparts, with Er and Ho dopant schemes showing the highest optical efficiencies.

Typically, naked (i.e., uncoated) REs are not suitable for biological applications due to their insolubility and tendency to agglomerate in aqueous solution. Additionally, naked REs are limited by a lack of functional groups for surface attachment of ligands or other biomolecules for actively targeted delivery, and may potentially have dose- and time-dependent cytotoxic effects. Many of the existing coating methods have issues of toxicity, poor stability in water, or require numerous steps to create functional groups on the particle surface for further conjugation to bio-molecules. A chemical functional group is defined as a submolecular structural motif, characterized by specific elemental composition and connectivity, that confers chemical reactivity upon the molecule that contains it. Examples of useful chemical functional groups include, without limitation: hydroxyl, carboxyl, amine, alkyl and thiol groups.

One embodiment of the invention involves coating of RE nanoparticles with albumin shells. Human serum albumin nanoshells (ANSs, alternatively termed albumin nanocarriers, ANCs) have been demonstrated to be bio-compatible with many cell types, exhibit long half life in vivo, are capable of delivering a number of biologically relevant compounds and have numerous functional entities available for conjugating ligands, antibodies and other peptides which can bind to specific molecular receptors. A ligand is a substance that forms a complex with a biomolecule, and binds to a site on a target protein or receptor. The ligand can also serve as a signal triggering molecule that initiates a casacade of biochemical reactions (e.g., cell death). Pharmaceutical formulations composed of human serum albumin are also in use clinically. For example, ABI-007 (ABRAXANE®, Abraxis BioScience Inc, Los Angeles, Calif.) is a commercial, albumin-bound paclitaxel delivery vehicle.

One embodiment of the invention is directed to REs encapsulated within an albumin nanoshell structure. In doing so it is possible to impart to the REs many of the benefits afforded by the ANS system. Once encapsulated, it is possible to functionalize the composite nanoparticle ((RE)ANS) with the cyclic arginine-glycine-aspartic acid (cRGD) tripeptide to examine the tissue targeting and biophotonic properties of the nanocomposites. The composite nanoparticles are observed to be highly biocompatible in vitro, as evidenced by lack of cytotoxicity, and are capable of selectively targeting cancer cell lines that exhibit higher expression of cancer-specific integrin markers, and amenable to fluorescence imaging with high fidelity.

Briefly, encapsulation in the form of (RE)ANS attenuated RE-induced cytotoxicity at 2.5 μg ml$^{-1}$ concentrations and significantly improved the biocompatibility of the rare earth nanoparticles at 250 mg ml$^{-1}$ after 24 h incubation with various types of human cells. One embodiment of the invention is directed to imaging cells incubated with (RE)ANS for approximately 5 days, after which time it is still possible to observe fluorescence from the cross-linked albumin, indicating that the albumin shell has maintained its integrity over this time course. The long-term cytotoxicity studies of nanoparticle exposure support these observations.

Functionalization of the particles with a targeting ligand was demonstrated with cyclic arginine-glycine-aspartic acid (cRGD) to selectively target cells that over-express the $\alpha_v\beta_3$ integrin receptor. The $\alpha_v\beta_3$ is an attractive targeting marker for locating and identifying cancer cells. Antagonists of $\alpha_v\beta_3$, such as the cRGD tripeptide motif, are capable of blocking both tumor cell metastasis and angiogenesis while providing a means of targeting cancer cells expressing the integrin.

Figure 3:
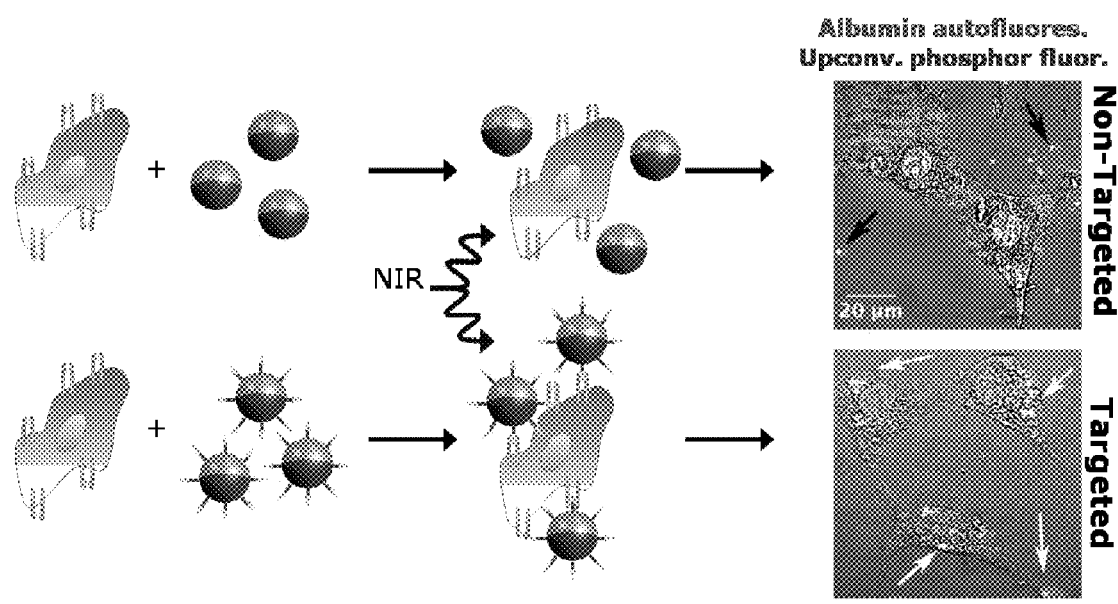
FIG. 3 illustrates a demonstration of human glioblastoma cells targeted without (top) & with (bottom) cyclic RGD presenting nanoparticles.

Upon surface modification of (RE)ANS with the cRGD tripeptide as a targeting ligand, the composite particles were demonstrated to be capable of selectively targeting both human glioblastoma and melanoma cell lines exhibiting higher expression of cancer-specific integrin markers, thereby demonstrating the preservation of the molecular potency of the tripeptide motif. (RE)ANS can be functionalized with various cyclic tripeptides using a standard cross-linking procedure conjugating the free amine groups on the albumin shell to thiol groups present on the ligands. (RE)ANS can be functionalized with either cRGD, which targets the integrin $\alpha_v\beta_3$, or, as a negative control, cyclic arginine-alanine-aspartic acid (cRAD) which does not have affinity for $\alpha_v\beta_3$. To confirm receptor specific targeting, (RE)ANS functionalized with cRGD were incubated with highly $\alpha_v\beta_3$ expressing U87-LUC and with low $\alpha_v\beta_3$ expressing A172 cells. Near infrared-excited fluorescent images of cRGD functionalized particles incubated with the U87 cells show particles distributed in a punctate pattern primarily throughout the cellular cytoplasmic space (FIG. 3). The U87 cells treated with non-functionalized or cRAD functionalized (RE)ANS showed little particle accumulation. Fluorescent images of the A172 cells incubated with cRGD particles demonstrated no detectable level of association of particles with cells, and appeared similar to the images of A172 cells treated with cRAD functionalized (RE)ANS or un-functionalized (RE)ANS. Quantification of fluorescence within the cell body was significantly elevated in U87-LUC cell line treated with cRGD functionalized (RE)ANS over 4 h in relation to that seen in the A172 cells.

Particles were also incubated with WM239A human melanoma cells, which are known to express high levels of the $\alpha_v\beta_3$ integrin. After 4 h, the (RE)ANS functionalized with cRGD accumulated around the WM239A cells whereas non-functionalized and cRAD conjugated particles showed low levels of cellular association, as was seen with the U87-LUC cells. Further, cRGD functionalized particles exhibited significantly more cellular internalization compared with non-functionalized particles during the same incubation times, which was confirmed by electron microscopy.

A bio-benign and tissue-targetable composite comprising nano scale and submicroscopic scale rare earth doped particles encapsulated in polypeptides (e.g., human serum albumin), polysaccharides or polymers was imbued with superior biophotonic properties, specifically related to emission in the visible (400 to 700 nm) and shortwave infrared (SWIR) window (1000 to 2500 nm) when excited in the near infrared (NIR) window (700 to 1000 nm).

The present invention provides the ability to be optically detected through the NIR excitation of the rare earth-containing particles to generate SWIR emission using low power (<2 W) excitation sources. Both the NIR and SWIR windows have very favorable biomedical optical characteristics, such as the ability to penetrate deeper than visible or UV radiation through biological tissue with minimal scattering and generating low background autofluorescence. NIR and SWIR radiation are also considered to be safe and non-phototoxic, while the composite formulation mitigates the intrinsic cytotoxic properties of RE particles.

The excitation and emission wavelengths of these composites can be tuned by controlling the dopant and host chemistry of rare earth-containing particles, and the density and type of rare earth-containing particles encapsulated by the polypeptide or polymer. The rare earth-containing particles that are incorporated within the composites can be of different sized (e.g. nanoscale or microscale) and morphologies (e.g. spheres, rods, platelets, prisms, cubes, acicular). The absorption and emission properties of rare earth-doped phosphors can be tailored by controlling the local environment, such as site symmetry, crystal field strength and electron-phonon interaction strength of rare earth dopants (see FIG. 1). Halide hosts (e.g. $NaYF_4$, $YF_3$, $LaF_3$, $CeF_3$, $CaF_2$ and $CsCdBr_3$) are favored for their low phonon energies that minimize non-radiative losses to enable intense SWIR emissions. Phonon energy ranges from 160 to 1400 cm$^{-1}$. $CsCdBr_3$ is one of the preferred host materials, with a phonon energy of 160 cm$^{-1}$. The higher phonon energy hosts have less bright emissions, or the emission can be absent altogether. Those skilled in the art are able to predict which combinations of host and rare earth element will be brighter. For example, the 1.3 micrometer emission is absent in oxides, but present in fluoride host materials. However a 1.5 micrometer emission can be found in both oxide and fluoride hosts. For the purposes of the present invention, $CeF_3$ is a preferred host.

While most rare earth elements can be excited to some extent by NIR light and emit to some extent in the SWIR window, rare earth-doped particle phosphors doped with ytterbium (Yb) or neodymium (Nd), and one or more elements selected from thulium (Tm), erbium (Er), praseodymium (Pr), dysprosium (Dy) and holmium (Ho) are preferred. In certain embodiments, suitable rare earth dopant schemes include Nd, Nd—Tm, Yb—Er, Yb—Tm, Yb—Pr and Yb—Ho. Furthermore, combinations of more than two rare earth dopants can be used, which include without limitation the following: Yb—Er—Tm, Yb—Pr—Tm—Er, Yb—Ho—Pr and Yb—Ho—Tm. In certain particularly preferred embodiments the host is $CeF_3$ and the rare earth element is selected from the group consisting of Pr, Nd, Yb, Er and combinations of two or more thereof. In addition, an undoped shell (>1.5 nm) surrounding the rare earth doped host may be used to reduce any emission quenching effects that typically arise from surface chemical functional groups (e.g. hydroxyl or alkyl).

The aqueous stability, particle dispersion/solubility, biocompatibility and functionality can be tailored by encapsulating rare earth nanoparticles with suitable macromolecules (e.g. deoxyribonucleic acid, ribonucleic acid, proteins, glycoproteins), polypeptides, polysaccharides or polymers. Some factors that will affect the dispersion or solubility of these composites are the chemical functional group expressed on the surface, and the hydrophilicity and surface charge of the polypeptides and polymers. In addition, the size of the composites can be varied by controlling the polypeptide or polymer coating on the REs (forming differently sized (RE)ANS) to further modulate the in vivo biodistribution. Closely tied to this modification is varying the size of the RE particles themselves, in order to regulate biodistribution and clearance. For example, the albumin coating on the rare earth-containing particles enables greater and improved bioavailability and biodistribution when introduced into a mouse displaying melanoma lesions. These composites can be of different sizes (e.g. nanoscale or microscale) and morphologies (e.g. spheres, rods, platelets, prisms, cubes, acicular).

Examples of suitable macromolecules, polypeptides, polysaccharides or polymers that could impart similar benefits as seen with albumin include without limitation, poly-L-lysine, poly-d-lysine, poly-ethylene glycol [PEG], poly-2-hydroxyethyl aspartamide, poly(d,l-lactide-co-glycolide) [PLGA], poly(methyl methacrylate) [PMMA], poly(N-isopropylacrylamide), poly(amidoamine) [PAMAM], polyethyleneimine, poly lactic acid, polycaprolactone, dextran, alginates, chitosan, transferrin, collagenase and gelatin. The macromolecules, polypeptides, polysaccharides or polymers are attached to rare earth-containing particles through either physical or chemical bonds (e.g., covalent, van der Waals, ionic, electrostatic, hydrogen bonds). Encapsulation techniques can include coacervation, coprecipitation, solvent evaporation, interfacial polymerization, emulsion, and hot melt processes. The method of executing the formulation is crucial to the final composite properties and function.

These composites can be further modified through the conjugation of compounds such as antibodies and peptides, which can target tumor receptors, as well as serve as a carrier of various therapeutic agents. Upon administration in vivo, the composites are distributed throughout the organism, with the targeting ligands directing distribution to the desired target site. A plurality of targeting ligands that target a plurality of receptors can be employed, thereby increasing the specificity of delivery to both the site and the specific cells or tissues at the site. Examples of targeting ligands include, without limitation: (1) Herceptin, which preferentially binds to the HER2/neu and folate receptors; (2) Glutamic acid-Proline-Proline-Threonine (EPPT) peptide, which preferentially binds to underblycosylated MUC-1 tumor antigen (uMUC-1), a common feature of numerous epithelial cell adenocarcinomas of breast, pancreas, colon/rectum, lungs, prostate, and stomach. The adaptability of the ligand or antibody conjugation procedure means that the type, number and combinations of targeting moieties on the surface of (RE)ANS can be modified easily, further improving their tumor localization and influencing their biodistribution. Besides detecting primary tumor sites, these composites can be tailored by modifying the surface chemistry to enable identification of secondary or metastatic tumor locations and/or circulating cells and lesions. Finally, the excitation and/or emission wavelengths of the REs can be used for the purposes of eliciting a therapeutic response, such as with releasing a therapeutic agent or triggering the activation of a therapeutic agent within the (RE)ANS.

Applications

Contrast Agent for Non-Invasive Medical Imaging Using Non-Ionizing, Low Energy Sources Cross-sectional 2-dimensional (2D) or 3-dimensional (3D) images of an object around a single axis of rotation can be generated using current medical imaging techniques like x-ray computed tomography (CT) and magnetic resonance imaging (MRI). Harmful side effects associated with the use of the high-energy radiation sources have limited its utility in medical diagnostics. Besides using high-energy radiation sources, intravascular contrast agents are required for both imaging modalities to improve the image quality (signal and resolution). The contrast agents are necessary to differentiate between adjacent soft tissues and organs, or to distinguish diseased tissue, such as a tumor mass, from the surrounding normal tissues. However, most current contrast agents have several limitations, including short imaging times due to rapid renal clearance, renal toxicity, allergic reactions, and vascular permeation.

In one embodiment of the invention, using a low photon energy, non-ionizing infrared light source and exploiting the NIR and SWIR biological windows, infrared imaging potentially offers a significantly safer and less invasive route to providing images of the body, its organs, and other internal structures for medical diagnostic purposes. However, for infrared imaging technology to be implemented, contrast agents to distinguish the various tissues, organs and tumor masses are needed. Having the infrared emitting composites introduced here will enable the successful implementation of infrared imaging. Furthermore, the infrared-emitting composites can also enable the non-invasive monitoring of the treatment of tumors, and provide details on the tumor architecture (e.g., vascular density).

In a further embodiment of the invention, color contrast or "multi-color" imaging can be enabled by utilizing composites that emit at different wavelengths. Color contrast is achieved by encoding the composites with different types of rare earth-containing particles that will provide each composite with a different emission wavelength. In addition, each differently-emitting composite is tailored with varying surface chemistries to direct the composite to a specific site of interest and thus enable assignment of different colors to each site. Subsequently, the "multi-color" imaging system will enable rapid identification of various sites of interests (e.g., dead vs. healthy tissues, diseased vs. healthy tissues, benign vs. malignant) simultaneously.

Image-Guides Interventions (Surgical and Non-Surgical)

In one embodiment of the invention, imaging techniques can be used to guide the insertion of small instruments and tools through the body to identify and treat a medical disorder without requiring conventional surgery. The image-guided procedures may be conducted for either diagnostic (e.g., angiogram) or treatment (e.g., angioplasty) purposes. The infrared-emitting composites can be injected to serve as vascular tracing agents to better guide surgeons performing these procedures. Images can be collected over the course of the procedure itself to provide real time information on the vasculature, and consequently significantly reduce the risk of potential undesirable complications.

Dual Functionality as Imaging Contrast Agent/Probe and a Drug Carrier

In another embodiment of the invention, the infrared-emitting composites can also serve as a drug carrier. Drug release can be either controlled by degradation rate (i.e. crosslinking density) of polymer/polypeptide or triggered by visible wavelength emissions from rare earth nanoparticles. Together with the use of the infrared imaging technology, the drug carrier penetration and treatment efficacy can be monitored. This can lead to rapid, longitudinal evaluation of drug carrier properties which can be used to optimize carrier design.

Drug delivery carriers such as coated nanoparticles strive to improve the bioavailability and, ultimately, the therapeutic action of a drug through a number of means. Drug carriers aid in increasing the aqueous solubility of poorly soluble drugs, reducing drug clearance by the reticuloendothelial system and offering a surface which can be modified with disease-targeting moieties minimizing systematic drug distribution, and ultimately leading to enhanced drug concentration at a diseased site. However, engineering an effective drug delivery vector requires an understanding of how a carrier's behavior and biodistribution in vivo are influenced by their design features. Enabling drug carriers to be visualized and subsequently tracked in real-time in vivo would provide researchers with a more thorough understand of these parameters and lead the way towards rationally engineered drug delivery.

Coatings, such as albumin nanoshells, have been shown to be capable of encapsulating and releasing small molecule drugs (<800 Da, organic compounds), nucleic acid polymers (such as antisense oligonucleotides, short interfering RNA, aptamers, etc.), plasmids, proteins and peptides, antibodies and polymers to numerous cell lines and in vivo models.

In a further embodiment of the invention, in addition to visualization, the visible wavelength emission of the rare earth nanoparticles can be used as a stimulus to induce structural or chemical changes within the drug delivery carrier or drug itself, enabling release and activation of the therapeutic agent. Designing drug carrier with energy- or light-responsive material coupled to rare earth nanoparticles could enable release and therapeutic action to be triggered and controlled in an on-off manner at diseased sites.

Dual Functionality as Imaging Contrast Agent/Probe and Gene Carrier

In another embodiment of the invention related to the drug carrier functionality, the infrared-emitting composites can be further employed as a gene carrier. In a potential disease treatment method, genes are inserted, altered, or removed to correct defective genes that are responsible for disease development Undesired side effects and safety concerns associated with viral vectors, such as acute immune response, immunogenicity, and insertion mutagenesis, have limited the application of gene therapy. Using non-viral vectors provides a relatively safe approach to increase or decrease the expression of a specific gene using DNA or antisense sequences. For gene delivery using composites, the extended long chain deoxyribonucleic acid (DNA) or ribonucleic acid (RNA) molecules are condensed to reduce the occupied spatial volume. Surface modification techniques are used to introduce chemical functional groups to enable particles to tightly bind with plasmid DNA and serve as a gene delivery carrier. Using the composites as a gene delivery carrier also prevents DNA from being degraded by environmental enzymes.

Dual Functionality as Imaging Contrast Agent/Probe and Agent for Photodynamic Therapy Typically, photodynamic therapy (PDT) is a minimally invasive treatment that destroys target cells in the presence of oxygen when visible light irradiates a photosensitizer (e.g., porphyrins), generating highly reactive singlet oxygen that then attacks the cellular target. The use of photosensitizers excited by visible light has thus far limited the use of PDT to tissues accessible with a light source. Current clinical applications include the treatment of solid tumors of the skin, lungs, esophagus, bladder, head, neck, and the like. In another embodiment of the invention, the visible wavelength emissions from rare earth-containing particles can be used for the purposes of eliciting a therapeutic response, such as with releasing a therapeutic agent or triggering the activation of a therapeutic agent within the (RE)ANS.

In a modification to conventional photodynamic therapy method, the phototoxic properties of high photon energy ultraviolet light are harnessed to enable similar therapeutic functions without the use of photosensitizers. The optical properties of rare earth-containing particles are tuned to favor ultraviolet emissions for the implementation of this concept.

Dual Functionality as Imaging Contrast Agent/Probe and Hyperthermia Agent

Local hyperthermia (or thermal ablation) is used to heat a very small area like a tumor. It creates very high temperatures that can kill cells, coagulate proteins, and destroy blood vessels. Radiofrequency ablation (RFA) which uses high-energy radio waves, is the most commonly used type of local hyperthermia. A thin, needle-like probe is introduced into the tumor for a short time (~10 to 15 min), where probe placement is guided using ultrasound or CT scans. The probe generates a high-frequency current that creates heat (~50-100° C.) and destroys the cells within a certain area.

In a further embodiment of the invention, the infrared-emitting composites can be used to deliver a therapeutic dose of heat by using moderately low exposures of externally applied near-infrared light. During hyperthermia therapy, the power of the near-infrared light incident upon a selected, desired area can be increased above the operating powers used to enable imaging. The efficacy of hyperthermia treatment can be modulated using these infrared-emitting composites by tuning the emissions from rare earth-containing particles to favor mid-infrared to far-infrared emissions that will generate heat when absorbed by tissues.

Tracking of Implantable Scaffolds and Devices and Sensors

In another embodiment of the invention, these composites can be used as a coating on medical implants, scaffolds or devices, such as neurovascular or endovascular stents, to allow the functionality of these implants to be monitored. By integrating the composites into biomedical devices, guided implantation of the devices can be performed (analogous to X-ray guided implantation of emerging radiopaque stents), and the progressive changes in the integrity and remodeling of implants can be monitored and evaluated in patients non-invasively.

Tissue Targeting for Detection of Pathologic Lesions and Plaques

In yet another embodiment of the invention, these composites can be developed with appropriate coating for preferential targeting to areas of vascular inflammation or fibrosis, and thus be used to guide the development of diagnostic strategies for detection of atherosclerotic plaques, fibrotic and diseased tissues and lesions and vascular aneurysms, to cite just a few examples, and to track the onset of emerging chronic conditions such as neurodegenerative disorders and metabolic diseases.

In Vivo and Ex Vivo Diagnosis and Disease Screening

In still another embodiment of the invention, these infrared-emitting composites can be further modified through the conjugation of compounds such as antibodies and peptides, which can target tumor receptors or diseased lesions. Subsequently, the modified composites will be localized at the targeted sites. The differential accumulation of particles will enable target-specific in vivo molecular imaging for early screening and diagnosis of diseases. Furthermore, certain circulating cells and pathogens (e.g., metastatic cancer cells, viruses, bacteria) can also be identified using the same concept.

The afore-mentioned embodiment can be further extended to the application of infrared emitting composites for ex vivo diagnosis and screening. Body fluids (e.g., blood, saliva, urine) are analyzed for certain circulating cells and pathogens (e.g., metastatic cancer cells, viruses, bacteria) using various biochemical and histochemical assay platforms. Examples of the biochemical assay testing platforms can include but are not limited to "lab-on-a-chip" and microarrays.

In addition, histopathological examination can be performed on tissue biopsies utilizing the infrared emission of the composites. Following composite administration into a patient or in vivo model, a sample of a tissue of interest can be removed, sectioned and viewed under using a conventional microscope to identify the presence and location of the nanoparticles. For example, the nanoparticle emission can be used as a tracer to identify where the particles are located in organs such as the liver, spleen and kidneys, as well as how widespread and homogenous they are in a tumor. Since vasculature can be visualized with the particles, irregular patterns in blood flow, commonly exhibited with tumors, can potentially be identified with this system.

One embodiment of the present invention is directed to a method of non-invasive infrared imaging, comprising the steps of:
(a) administering a composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and
(b) irradiating with infrared radiation,
wherein both excitation and emission spectra of the coated nanoparticles are in the infrared region.

Another embodiment of the invention is directed to a method of image-guided biomedical intervention, comprising the steps of:
(a) administering a composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and
(b) irradiating with infrared radiation,
wherein both excitation and emission spectra of the coated nanoparticles are in the infrared region.

Still another embodiment of the invention is directed to a method of drug tracking and delivery, comprising the steps of:
(a) administering a drug composition comprising infrared-emitting nanoparticles comprising rare earth elements, wherein the nanoparticles are encapsulated with a biocompatible matrix to form downconverting coated nanoparticles tuned to optimize short-wavelength infrared (SWIR) emission; and
(b) irradiating with infrared radiation,
wherein both excitation and emission spectra of the coated nanoparticles are in the infrared region.

Another embodiment of the invention is directed to a method of improving the biocompatibility and/or reducing the toxicity and/or side effects of a drug and/or imaging agent, comprising the step of encapsulating the drug and/or imaging agent with a biocompatible matrix.

Yet another embodiment of the invention is directed to a method of biologically targeting a drug and/or imaging agent, comprising the step of encapsulating the drug and/or imaging agent with a biocompatible matrix.

For any of the above methods, a preferred biocompatible matrix comprises human serum albumin (HSA). In addition, for any of the above methods, the biocompatible matrix can further comprise a pharmaceutical agent, and/or a targeting molecule which directs the coated nanoparticle to a biological target. A preferred targeting molecule comprises cyclic arginine-glycine-aspartic acid (cRGD) tripeptide.

For the methods comprising nanoparticles, the nanoparticles preferably comprise $CeF_3$ doped with one or more rare earth elements selected from the group consisting of Yb, Nd, Tm, Er, Pr, Dy and Ho. Most preferably the rare earth elements are selected from the group consisting of Pr, Nd, Yb and Er. In addition, for the methods comprising nanoparticles, the nanoparticles can further comprise one or more elements selected from the group consisting of Gd, La, Ce, Pm, Sm, Eu, Gd, Tb, and Lu. This allows for use as a multi-modal imaging agent. The multi-modal detection scheme can be selected from optical/MRI, or optical/PET with a radiolabel.

Yet another embodiment of the invention is directed to a composition for biomedical applications, comprising infrared-emitting nanoparticles comprising rare earth-elements, wherein the nanoparticles are encapsulated with a biocompatible matrix to form downconverting coated nanoparticles tuned to optimize short-wavelength infrared (SWIR) emission. Preferably the biocompatible matrix comprises human serum albumin (HSA). Also, the biocompatible matrix can further comprise a pharmaceutical agent, and/or a targeting molecule which directs the coated nanoparticle to a biological target. A preferred targeting molecule comprises cyclic arginine-glycine-aspartic acid (cRGD) tripeptide. As above, the nanoparticles preferably comprise $CeF_3$ doped with one or more rare earth elements selected from the group consisting of Yb, Nd, Tm, Er, Pr, Dy and Ho. Most preferably the rare earth elements are selected from the group consisting of Pr, Nd, Yb and Er. In addition, the nanoparticles can further comprise one or more elements selected from the group consisting of Gd, La, Ce, Pm, Sm, Eu, Gd, Tb, and Lu. This allows for use as a multi-modal imaging agent. The multi-modal detection scheme can be selected from optical/MRI, or optical/PET with a radiolabel.

EXAMPLES

Example 1. Small Animal SWIR-Imaging System Using NIR Excitation

Figure 4:
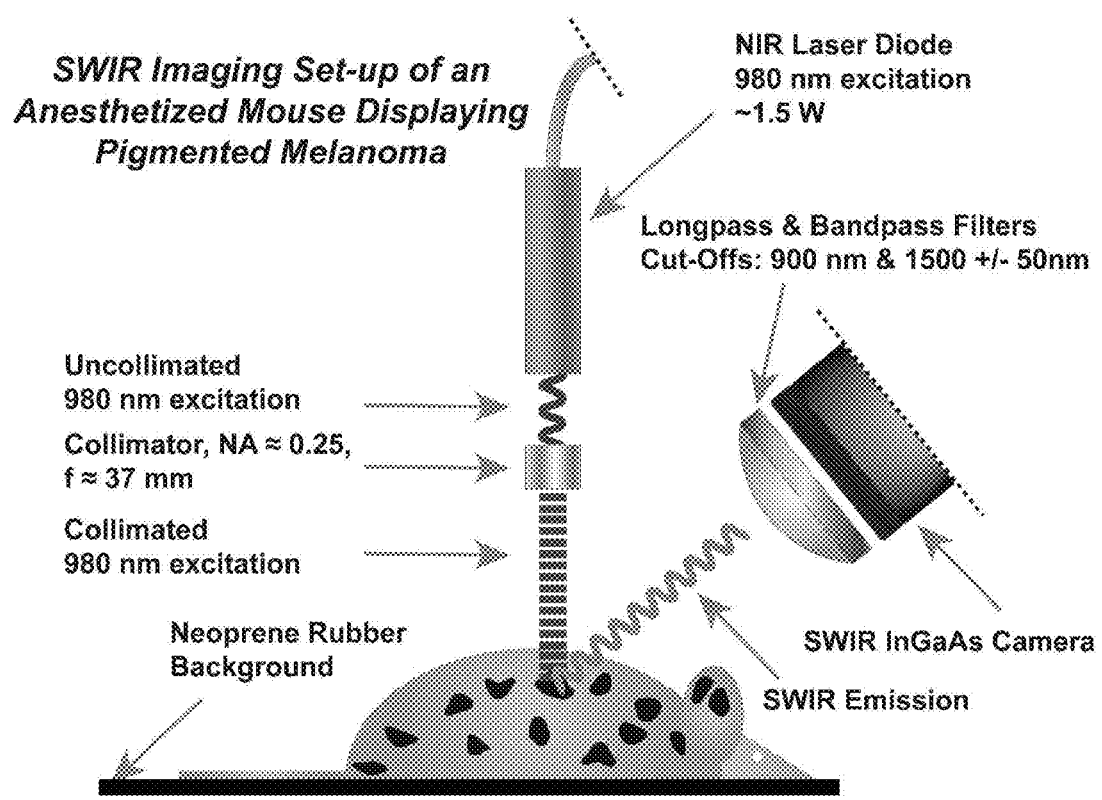
FIG. 4 illustrates a SWIR imaging set-up of an anesthetized mouse displaying pigmented melanoma following (RE)ANS injection.

A prototype of a small animal SWIR-imaging system was designed and built to demonstrate of the utility of our composites for non-invasive SWIR imaging. The in-house SWIR-imaging prototype consists of a fiber-coupled NIR laser photodiode which operates at 980 nm and 1.4-1.5 W, and a thermoelectric-cooled Indium Gallium Arsenide (InGaAs) SWIR camera with a detection range from 800 to 1700 nm (see FIG. 4). FIG. 4 shows a SWIR imaging set-up of an anesthetized mouse displaying pigmented melanoma following (RE)ANS injection. Excitation of the mouse was performed using a 980 nm laser diode equipped with a collimator operating at approximately 1.4-1.5 W. Emission was captured using a SWIR InGaAs camera equipped with two sets of filters (longpass-900 nm and bandpass-1500 nm+/−50 nm) to ensure the elimination of the excitation light from the captured images. Black Neo-prene rubber was used as the background for the mouse to rest on in order to provide an infrared black background in order to enhance the signal-to-noise ratio for the collected emission.

A collimator is attached to the excitation fiber to enable a uniform and constant excitation beam radius which is independent of the distance between source and animal subject. During the imaging, the excitation fiber is held at an arbitrary distance above the animal and slowly scanned across the animal's body. Any SWIR emissions are then simultaneously captured in real time by the SWIR camera that is positioned in a fixed height above the animal. These videos are captured at ~19-22 frames per second (i.e. detection exposure time ~45-53 msec). Optical filters were fitted onto the SWIR camera to eliminate detection of the MR excitation source to confidently determine that only the SWIR emissions were captured. An incandescent Xe flashlight was used to provide backlight to partially resolve the location of the mouse. Finally, black Neoprene rubber or a latex-paint-coated cardboard was used as the background surface on which the mouse is placed to reduce the amount of ambient reflected light and produce a favorable signal-to-noise ratio. Compared to another similarly functioning system which uses a 20 W pulsed NIR source and liquid nitrogen cooled SWIR camera with exposure times in the hundreds of milliseconds for the imaging of SWIR-emitting carbon nanotubes, the above prototype operates at significantly lower excitation power with better detector sensitivity.

Example 2. Detection of NIR-To-SWIR Fluorescence In Vivo

Figure 5:
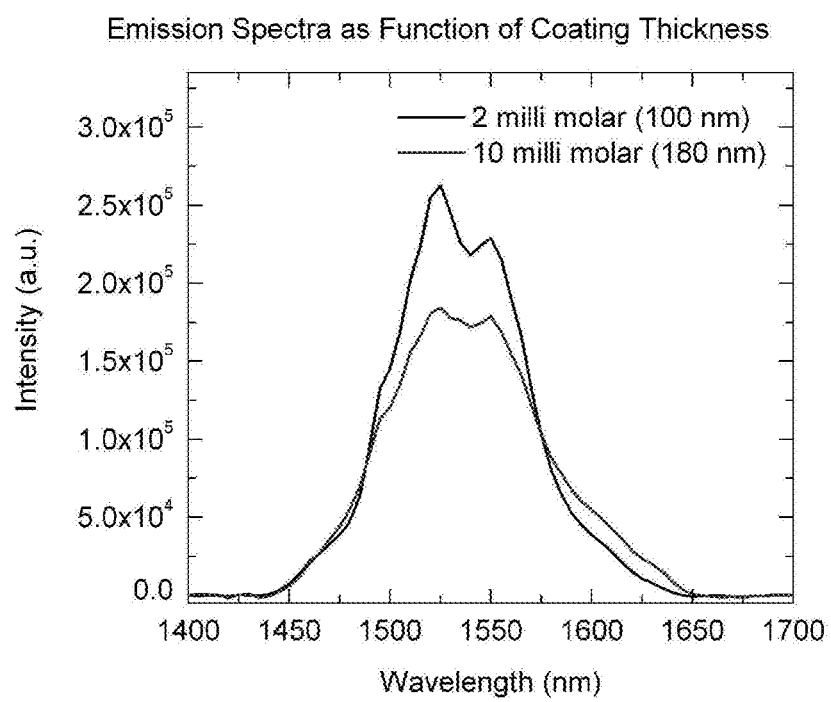
FIG. 5 displays the SWIR emission spectra of variously sized RE-ANS (synonymous to (RE)ANS) following 980 nm excitation.

Variously sized (RE)ANS were introduced through intraperitoneal and intravenous administration into rodent models. The nanoparticles were imaged using an SWIR camera to capture the SWIR emission of the particles following their fluorescent excitation at 980 nm. The SWIR emission around 1500 nm of the REs following NIR excitation was confirmed for the ANS-encapsulated composites of the RE's (FIG. 5). This is consistent with the previous reports that, in addition to the traditional "optical imaging window" of NIR between 650 to 950 nm, there lies another second "window" in the SWIR region of the spectrum between 1000 to 1700 nm mimicking the improved signal-to-noise ratios for seen in traditional NIR imaging.

Figure 6:
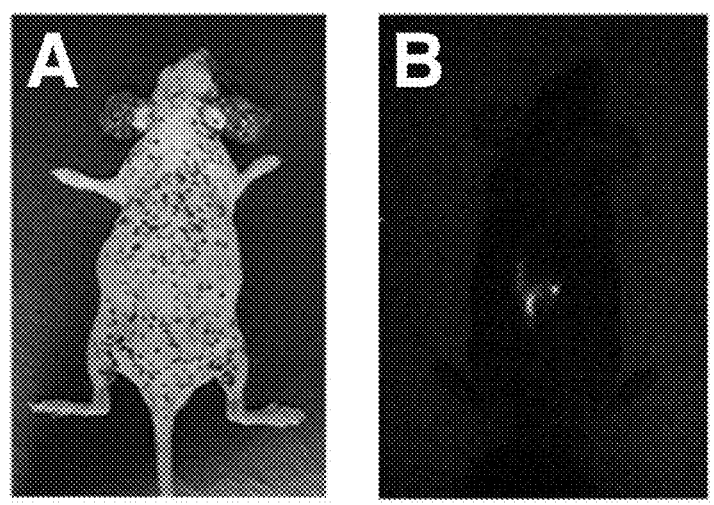
FIG. 6 shows a picture of a mouse exhibiting melanoma lesions injected with 100 μl of (RE)ANS (2.0 mg RE ml$^{-1}$) via the peritoneum and imaged for SWIR emission after 30 minutes.

In order to examine the biodistribution of the (RE)ANS, a melanoma model was used. These mice develop melanoma spontaneously around the ears, snout and anus followed by lesions on their skin and metastases in their lymph nodes. Many of these tumors become highly vascularized over time. Two strains of the mice were utilized: ones with highly pigmented melanoma lesions and ones without this distinguishing pigment. Using the SWIR emission of 100 nm (RE)ANS, the presence of the nanoparticles in tissues including liver, vasculature and tumors, was successfully identified in the mice expressing pigmented lesions following either intravenous (IV) or intraperitoneal (IP) injection of the nanoparticles (FIG. 6). During the SWIR imaging, no visible wavelength emissions were observed at the sites where SWIR emissions were observed. Any visible wavelength emissions were most likely attenuated by the skin, tissues or blood.

FIG. 5 displays the SWIR emission spectra of variously sized RE-ANS (synonymous to (RE)ANS) following 980 nm excitation. Both the 2 millimolar (100 nm) and 10 millimolar (180 nm) RE-ANSs display emission in the SWIR, indicating the RE emissive properties are retained after albumin encapsulation. FIG. 6 shows a picture of a mouse exhibiting melanoma lesions injected with 100 μl of (RE)ANS (2.0 mg RE ml$^{-1}$) via the peritoneum and imaged for SWIR emission after 30 minutes. A digital camera image of the mouse prior to injection show the black, pigmented lesions are located throughout the mouse body particularly on the ears and back (A). Numerous sites throughout the animal showed SWIR emission when the 980 nm excitation laser diode irradiated a particular region. Sites on the animal's back showed what appears to be emission of the nanoparticles in structures resembling vasculature (B), indicating the ability to rapidly screen and track nanoparticles bio-distribution in real time.

Thus, the proof-of-concept of the superior in vivo biophotonic properties of the nanocomposites of the invention has been established. This also demonstrates that albumin encapsulation enables greater biodistribution of the RE compared with the uncoated RE.

Example 3. Demonstration of Superiority of Biodistribution of RE-Composites Over Naked RE's Striking differences in biodistribution following IP injection of REs or (RE)ANS (FIG. 7) were observed. While the (RE)ANS in the peritoneal cavity progressively diminish from the site of injection over time, accumulating and clearing from different organs and tumors, uncoated RE particles do not distribute from the site of injection even after 7 days. After dissecting the animal most of the uncoated REs were found to be located in the IP cavity sac, a highly vascularized structure lining the abdomen and known to be the first point of entry into the blood stream of compounds introduced via IP injection (FIG. 8). This confirms that albumin encapsulation facilitates the absorption of the coated RE particles into the bloodstream, enabling improved biodistribution compared to the REs alone.

Figure 7:
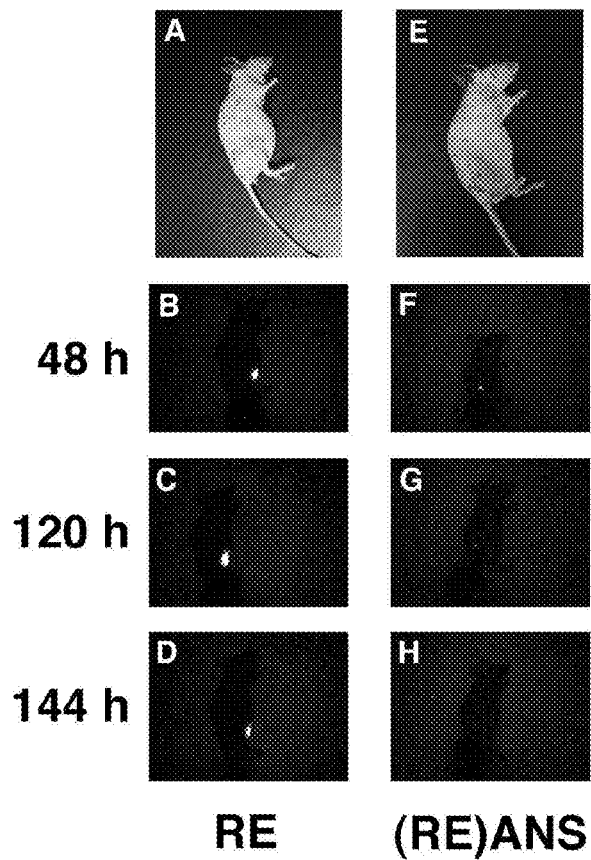
FIG. 7 shows pictures of mice exhibiting melanoma lesions injected with 100 μl of REs and (RE)ANS (2.0 mg RE ml$^{-1}$) via the peritoneum.
Figure 8:
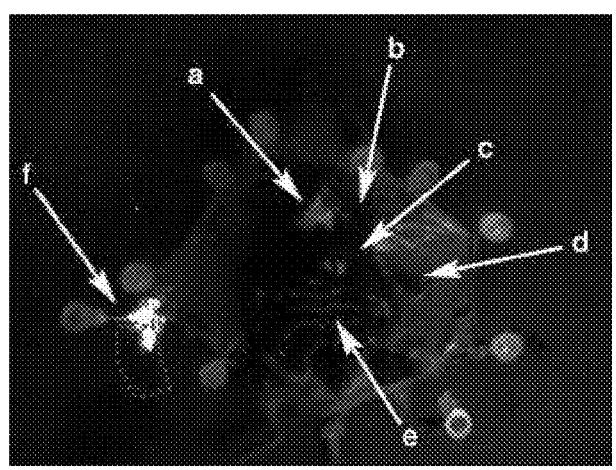
FIG. 8 shows a picture of a mouse exhibiting melanoma dissected after 168 h following IP injection of REs (100 μl at 2.0 mg RE ml$^{-1}$).

FIG. 7 shows pictures of mice exhibiting melanoma lesions injected with 100 μl of REs and (RE)ANS (2.0 mg RE ml$^{-1}$) via the peritoneum. Digital camera images of the mice prior to injection show the black, pigmented lesions are located throughout the mice bodies particularly on their ears, anus and back (A, E). After 48 h following IP injection, both mice injected with REs (B) and (RE)ANS (F) exhibit SWIR emission around the site of injection when the 980 nm excitation laser diode irradiates the region. Over time, however, the emission of the (RE)ANS diminishes (G-H), indicated the nanoparticles are clearing the injection site, in contrast to the REs (C-D), which appear to remain at the site of injection. FIG. 8 shows a picture of a mouse exhibiting melanoma dissected after 168 h following IP injection of REs (100 µl at 2.0 mg RE ml$^{-1}$). Although most organs such as the lungs (a), heart (b), liver (c), lymph node(s) (d) and intestines (e) do not exhibit SWIR fluorescence, the intraperitoneal cavity sac (f and structure dissected from the animal outlined), a highly vascularized structure lining the abdomen and known to be the first point of entry into the blood stream of compounds introduced via IP injection. This indicates that the REs are unable to enter into circulation following their injection into the peritoneum.

Example 4. Tissue Targeting and Multifunctional Drug Carrier Platforms

Figure 11:
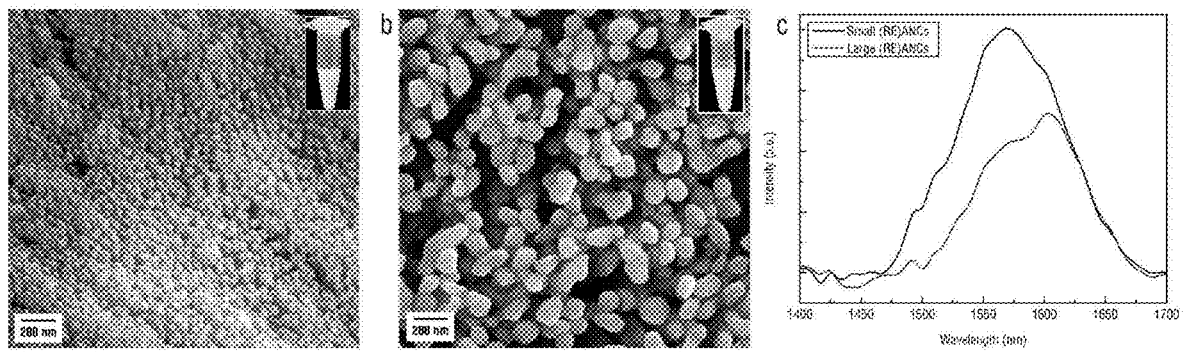
FIG. 11 displays physical and optical properties of (RE) ANCs.

Adjusting the particle size of the REs and the presentation of specific receptor targeting moieties on the (RE)ANS can lead to improved and directed tissue-targeting. FIG. 11 shows physical and optical properties of (RE)ANCs. SEM images of both small (a) and large (b) (RE)ANCs show uniform sub-100 nm spherical particles. Both sizes of (RE) ANCs retain the SWIR emission of the encapsulated REs, exhibiting peak emission between 1550-1600 nm following 980 nm excitation (c). Based on microscopy imaging, small and large lyophilized (RE)ANCs exhibit an average size of 46 nm and 100 nm which appears to swell when hydrated to 100 and 280 nm, respectively. DLS measurements confirm a low polydispersity and heterogeneity of size. Furthermore, both formulations show negative zeta potentials in PBS (pH 7.4), with the HSA content increasing for larger (RE) ANCs±S.D. Various pharmacologic factors and/or targeting molecules may be incorporated into the (RE)ANS thus creating a drug delivery vector that can be tracked in vivo using NIR-to-SWIR optical imaging.

One embodiment of the invention is directed to incorporating various cancer therapeutic agents into the (RE)ANS coating. Monomeric albumin is known to contain two primary drug binding sites as well as numerous secondary binding sites. It is thus possible to utilize these intrinsic sites to confine compounds known to be effective against cancers such as melanoma onto the (RE)ANS. The maximum drug loading quantities for compounds such as curcumin (FIG. 9), a naturally derived compound shown to have therapeutic properties in a variety of cancers, and BAY 36-7620, a receptor antagonist shown to be effective against melanoma, have been determined. Furthermore, it has been demonstrated that the in vitro efficacy of these drugs is retained following association with the nanoparticles (FIG. 10). Thus, the optical properties of the (RE)ANS can be used to track the delivery of drug in vivo, enabling longitudinal evaluation of drug biodistribution and delivery optimization.

Figure 9:
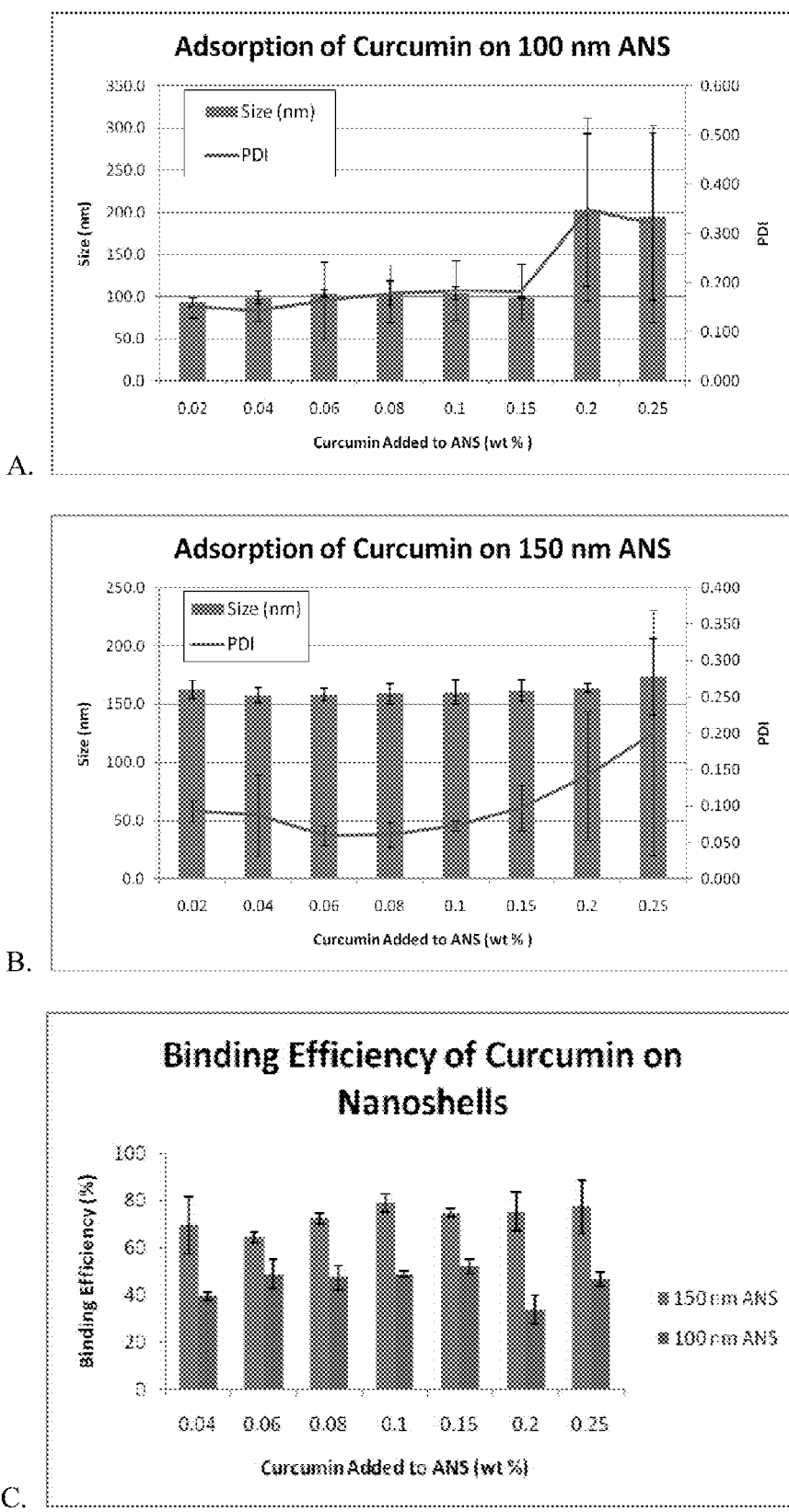
FIG. 9 shows drug loading of variously sized ANS with curcumin (A, B) and binding efficiency of loading (C).
Figure 10:
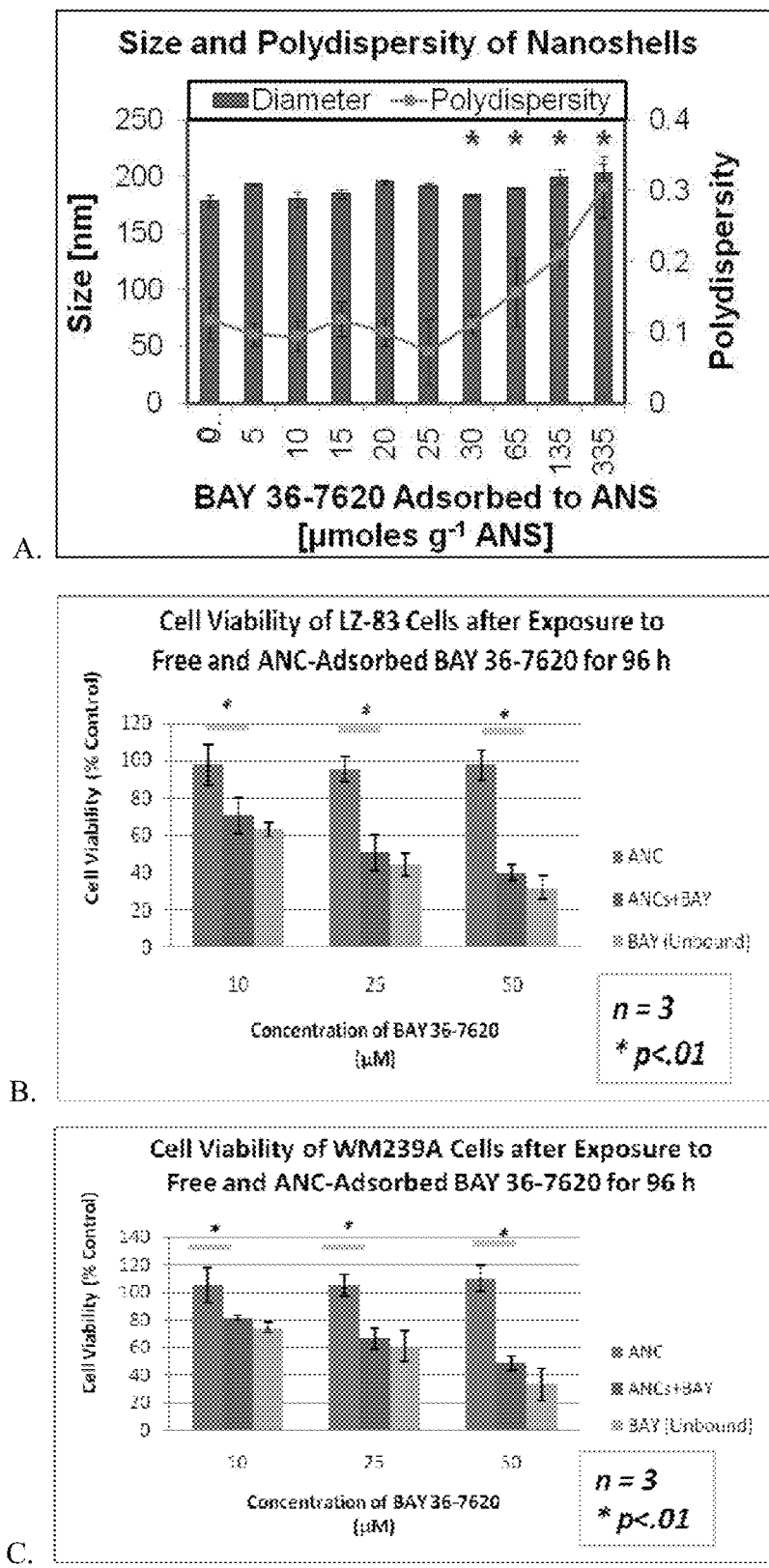
FIG. 10 shows drug loading of ANS with BAY 36-7620 (A) and cytotoxicity assay of LZ-84 murine (B) and WM239A human (C) melanoma cells exposed to ANSs with and without BAY 36-7620, a glutamate receptor antagonist shown to induce cell death in numerous melanoma cell lines.

FIG. 9 shows drug loading of variously sized ANS with curcumin (A, B) and binding efficiency of loading (C). Both 100 and 150 nm ANS begin to display progress increase in polydispersity when loaded with >0.15 wt % of curcumin, indicating maximum loading. This corresponds to greater than 50% binding efficiency for the 100 nm ANS and approximately 75% efficiency for the 150 nm ANS. FIG. 10 shows drug loading of ANS with BAY 36-7620 (A) and cytotoxicity assay of LZ-84 murine (B) and WM239A human (C) melanoma cells exposed to ANSs with and without BAY 36-7620, a glutamate receptor antagonist shown to induce cell death in numerous melanoma cell lines. Through sizing and polydispersity measurements performed using DLS, 25 µmoles BAY 36-7620 g$^{-1}$ nanoshells can be adsorbed onto the surface of the nanoshells. When exposed to melanoma cell lines, although ANSs alone do not induce notable cytotoxicity in the melanoma cell lines, the ANSs loaded with BAY 36-7620 show comparable cytotoxicity to BAY 36-7620 alone after 96 h, indicating that the drug's activity is retained even after incorporation into the nanoparticles.

Figure 12:
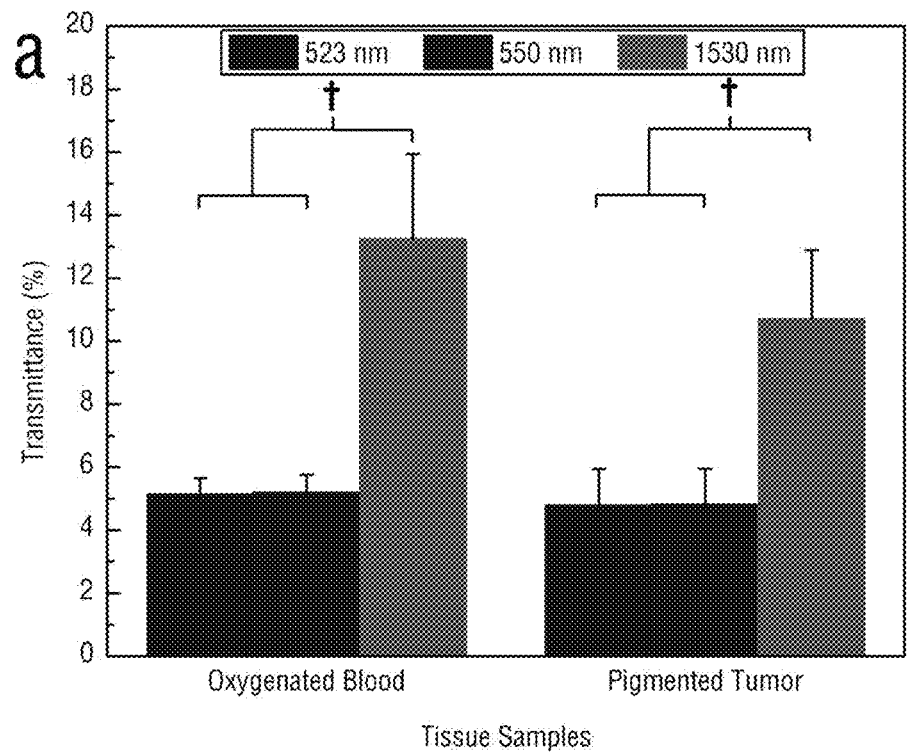
FIG. 12 shows the transmission efficiency and absorbance of SWIR and visible RE emissions through blood and pigmented tumor samples.
Figure 12:
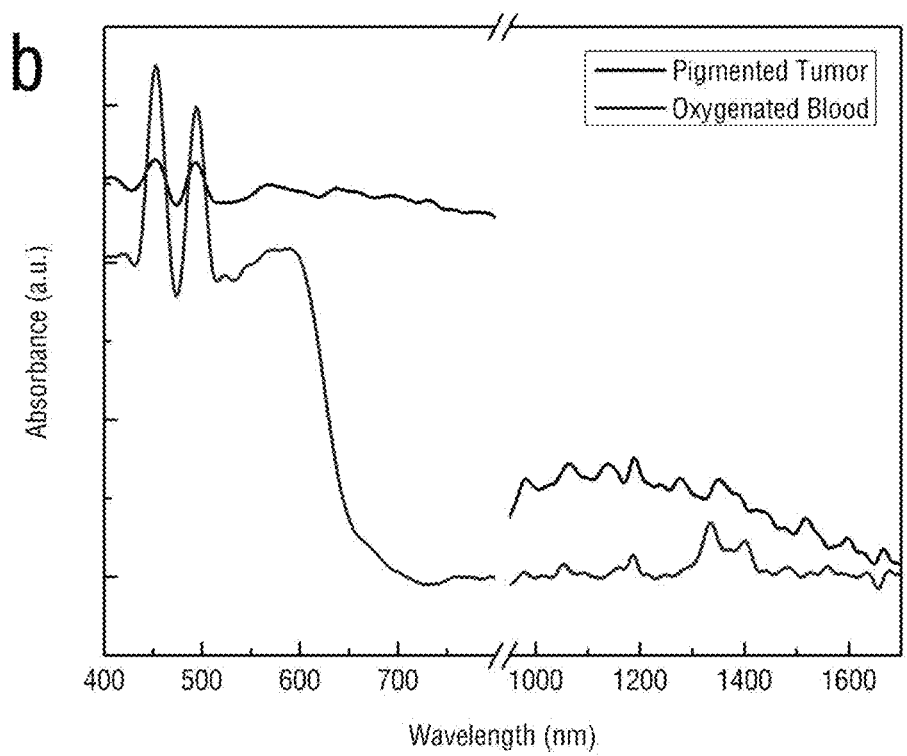

FIG. 12 shows the transmission efficiency and absorbance of SWIR and visible RE emissions through blood and pigmented tumor samples. RE(Er) nanoparticles with emission in both the visible and SWIR transmit through blood and tumor samples approximately 3- and 2-fold greater, respectively, in the SWIR (1530 nm) than compared to their peak emissions in the visible (523 and 550 nm) (a). Furthermore, the absorbance of the melanin present in the tumors exhibits a minimum beyond 900 nm, while blood shows an absorbance minimum beyond 700 nm (b). Note the break in the spectra from 800 to 900 nm is due to the spectroscope detector change. Shaded region represents the NIR while blue the SWIR.±SE; †, P<0.01 Student's t-test.

Furthermore, the natural ability of albumin to bind to multiple classes of compounds opens the possible for simultaneous, multi-drug delivery. Numerous therapeutic compounds have been shown to work in a synergistic fashion when combined with other therapeutic agents, eliciting greater responses than if the drugs were acting alone. Delivering two or more drugs simultaneously via the nanocarriers, in which the drugs act on multiple or individual targets, may provide a greater disease therapy.

The above examples, taken together with the following claims are intended to be representative of the invention, and are not intended to limit it in any way.

We claim:
1. A composition for biomedical applications, comprising a plurality of infrared-emitting particles comprising rare earth-elements that emit in the short-wavelength infrared (SWIR) spectrum, wherein said infrared-emitting particles are directly encapsulated with a shell comprising one or more of polypeptides, polysaccharides, and biocompatible polymers, to form spherical downconverting microcapsules comprising a plurality of said infrared-emitting particles, wherein said infrared-emitting particles have a size between 2 nm and 10 micrometers, wherein said microcapsules have a capsule size between 10 nm and 100 micrometers, and wherein said infrared-emitting particles have a relative size permitting the plurality of infrared-emitting particles to be loaded into said microcapsules.

2. The composition of claim 1, wherein said one or more of the polypeptides, polysaccharides and biocompatible polymers of said shell is selected from the group consisting of poly-L-lysine, poly-D-lysine, polyethylene glycol, poly-2-hydroxyethyl aspartamide, poly(D,L-lactide-co-glycolide), poly(methyl methacrylate), poly(N-isopropylacrylamide), poly(amidoamine), polyethyleneimine, poly lactic acid, polycaprolactone, dextran, alginates, chitosan, transferrin, collagenase and gelatin.

3. The composition of claim 1, wherein said shell comprises the biocompatible polymer polyethyleneimine.

4. The composition of claim 1, wherein said shell further comprises a pharmaceutical agent.

5. The composition of claim 1, wherein said shell further comprises one or more targeting molecules which direct said encapsulated infrared-emitting particles to a biological target.

6. The composition of claim 1, wherein said infrared-emitting particles comprise $CeF_3$ doped with one or more rare earth elements selected from the group consisting of Yb, Nd, Tm, Er, Pr, Dy and Ho.

7. The composition of claim 1, wherein said infrared-emitting particles further comprise one or more elements selected from the group consisting of La, Ce, Pm, Sm, Eu, Gd, Tb, and Lu.

8. The composition of claim 1, wherein said infrared-emitting particles are a factor of about 10 or more smaller than said microcapsules.

9. The composition of claim 1, wherein the infrared-emitting particles loading in said microcapsules ranges from 0.004 wt % to 94 wt %.

10. The composition of claim 9, wherein the infrared-emitting particles loading in said microcapsules ranges from about 10 wt % to about 40 wt %.

11. A method of non-invasive infrared imaging of a biological object, comprising the steps of:
   (a) administering to a biological object the composition of claim 1;
   (b) irradiating said biological object with infrared radiation; and
   (c) capturing infrared emission spectral images of said encapsulated infrared-emitting particles in said biological object;
   wherein both excitation and emission spectra of the encapsulated infrared-emitting particles are in the infrared region.

12. A method of drug tracking and delivery in a biological object, comprising the non-invasive infrared imaging method of claim 11 wherein said composition further comprises a drug.

13. The method of claim 11, wherein said shell further comprises a pharmaceutical agent.

14. The method of claim 11, wherein said shell further comprises one or more targeting molecules which direct said encapsulated infrared-emitting particles to a biological target.

15. The method of claim 11, wherein said infrared-emitting particles comprise $CeF_3$ doped with one or more rare earth elements selected from the group consisting of Yb, Nd, Tm, Er, Pr, Dy and Ho.

16. The method of claim 11, wherein said infrared-emitting particles further comprise one or more elements selected from the group consisting of La, Ce, Pm, Sm, Eu, Gd, Tb, and Lu.

17. The method of claim 11, wherein said microcapsules have a capsule size between 10 nm and 300 nm.

18. The method of claim 11, wherein said microcapsules have a capsule size between 100 nm and 300 nm.

19. The method of claim 11, wherein said infrared-emitting particles are a factor of about 10 or more smaller than said microcapsules.

20. The method of claim 11, wherein the infrared-emitting particle loading in said microcapsules ranges from 0.004 wt % to 94 wt %.

21. The method of claim 20, wherein the infrared-emitting particle loading in said microcapsules ranges from about 10 wt % to about 40 wt %.

* * * * *

UNITED STATES PATENT AND TRADEMARK OFFICE
CERTIFICATE OF CORRECTION

PATENT NO. : 10,814,017 B2  
APPLICATION NO. : 16/378792  
DATED : October 27, 2020  
INVENTOR(S) : Dominik J. Naczynski et al.

Page 1 of 1

It is certified that error appears in the above-identified patent and that said Letters Patent is hereby corrected as shown below:

In the Specification

At Column 1, Line number 18, please delete the paragraph following the subtitle "STATEMENT REGARDING FEDERALLY SPONSORED RESEARCH OR DEVELOPMENT" and add the following:
This invention was made with government support under grant number 0609000 awarded by the National Science Foundation and grant number N00014-08-1-0131 awarded by United States Office of Naval Research. The government has certain rights in the invention.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*